Figure 1A:
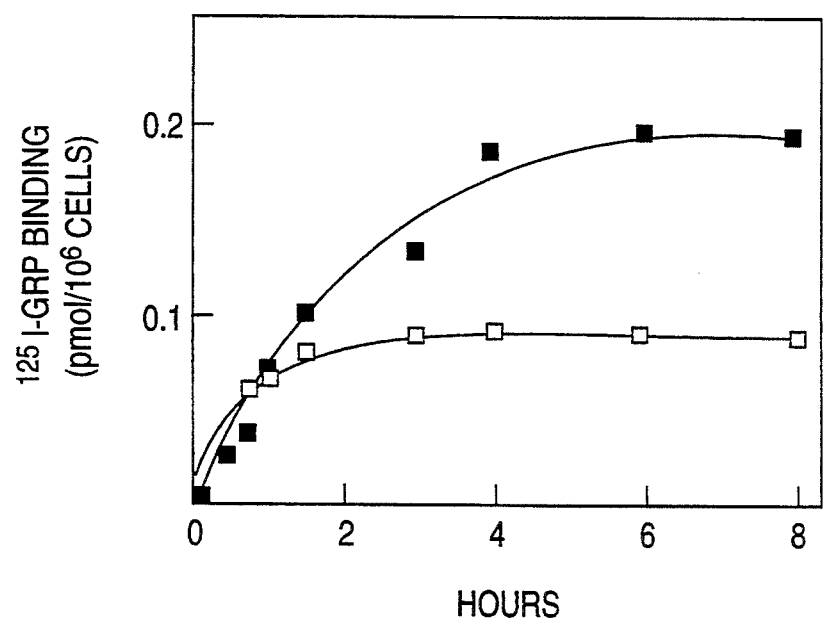

United States Patent [19]

Rozengurt et al.

[11] Patent Number: 5,441,935
[45] Date of Patent: Aug. 15, 1995

[54] GROWTH FACTOR RECEPTORS

[75] Inventors: Enrique Rozengurt; Ian Zachary; Penella Woll, all of London, England

[73] Assignee: Imperial Cancer Research Technology Ltd., London, England

[21] Appl. No.: 939,587

[22] Filed: Sep. 3, 1992

Related U.S. Application Data

[63] Continuation of Ser. No. 814,064, Dec. 23, 1991, abandoned, which is a continuation of Ser. No. 411,536, Nov. 29, 1989, abandoned.

[30] Foreign Application Priority Data

Mar. 31, 1987 [GB] United Kingdom ............... 8707607
Nov. 25, 1987 [GB] United Kingdom ............... 8727638

[51] Int. Cl.$^6$ .................. A61K 37/02; C07K 15/00; G01N 33/574; G01N 33/566
[52] U.S. Cl. .................. 514/15; 530/327; 435/7.21; 436/501; 930/21
[58] Field of Search ............ 435/7.21; 436/501; 514/15; 530/327; 930/21

[56] References Cited

U.S. PATENT DOCUMENTS 4,481,139 11/1984 Folkers et al. ............... 530/327
5,073,541 12/1991 Taylor et al. ............... 514/9

OTHER PUBLICATIONS

*Proc. Natl. Acad. Sci.* USA, vol. 85, No. 6, Mar. 1988, P. J. Woll et al. pp. 1859–1863.
*Proc. Natl. Acad. Sci.,* USA, vol. 82, Nov. 1985, I. Zachary et al. pp. 7616–7620.
*The Journal of Biological Chemistry,* vol. 262, No. 23, 15 Aug. 1987, The American Society for Biochemistry and Molecular Biology, Inc., (US), R. M. Kris et al. pp. 11215–11220.
*Acta Chemica Scandinavica,* vol. B40, 1986, K. Folkers et al. pp. 295–302 see table I, No. 1,4,10; table 2, No. 1,3,6; table 7, No. 1.
*The Journal of Biological Chemistry,* vol. 262, No. 9, 25 Mar. 1987, The American Society of Biological Chemists, Inc., (US), I. Zachary et al. pp. 3947–3950.
*Nature,* vol. 316, 29 Aug. 1985, F. Cuttitta et al. pp. 823–826, see page 826, column 1, lines 6–16.
*Biological Abstracts,* vol. 83, D. M. Cirillo et al., abstract No. 66775, & Mol. Cell. Biol. 1986, vol. 6, No. 12, pp. 4641–4649.
Cancer Research Supp.; 52 2737–2742 (1992).
*Eur. J. Biochem.,* 27:201–202 (1972).
Layton, et al., (1987) *J. Cell. Biochem.* vol. O (11) A, p. 32, A140.
Corps, et al., "A Peptide that inhibits the mitogenic stimulation of Swiss 3T3 cells by bombesin or vasopressin," Biochem. J. 231 (1985), 781–84.
Zacary et al., "A Substance P Antagonist Inhibits Specific Binding and Mitogenic Effects of Vasopressin and Bombesin-Related Peptides in Swiss 3T3 Cells," Biochem. Biophys Res Comm 137:135–141 (1986).
Layton et al., J. Cell Biochem Suppl (11) A:32 (1987).
Jensen et al., Nature 309:61–63 (1984).
Bepler et al., "In Vitro Growth Inhibition Of Human Small Cell . . . ," Cancer Research 47:2371–2375 (1987).
Gazdar et al., "Cell Lines As An Investigational Tool For The Study . . . ," Eur J Cancer Clin Oncol 21:815–824 (1985).
Koros et al., "Stability and Utility of The Unique Human Small Cell Carcinoma Line . . . ," Cancer Res 45:2725–31 (1985).

*Primary Examiner*—Michael P. Woodward
*Attorney, Agent, or Firm*—Morrison & Foerster

[57] ABSTRACT

A 75–85 Kd glycopolypeptide, capable of acting as a receptor for polypeptide of the bombesin type, is isolated from the surface of Swiss 3T3 cells. Certain antagonists and antibodies to the glycopolypeptide are described, the antagonists being of quite different structure to bombesin e.g. ∂D-Pro$^2$[-spantide, ∂D-Phe$^5$[-spantide and position 5 variants thereof. The antagonists and antibodies are of interest medically in that they are able to influence cell proliferation that occurs under the influence of the bombesin-like polypeptides.

3 Claims, 9 Drawing Sheets

GROWTH FACTOR RECEPTORS

This application is a continuation, of application Ser. No. 07/814,064, filed Dec. 23, 1991, abandoned, which is a continuation of Ser. No. 07/411,536, filed Nov. 29, 1989, abandoned.

This invention relates to antagonists to growth factor receptors and is particularly concerned with antagonists to bombesin receptors.

The amphibian tetradecapeptide bombesin (6) and mammalian peptides structurally related to bombesin, which include gastric releasing peptide (GRP) and the neuromedins (7 to 12) are growth factors which are believed to be implicated in the control of cell proliferation. Bombesin-like peptides are present in high concentrations in small cell lung carcinoma (18 to 21) where they could act as autocrine growth factors (22). The bombesin group of peptides interact in the cell with receptors but while a certain amount is known about the chemistry of the bombesin group of peptides, very little is known about the chemistry of the receptors of the bombesin-like peptides. In view of the involvement of the bombesin-like peptides in cell growth and the implications on cell growth of the presence or absence of bombesin/receptor interaction, a detailed study of the receptors is clearly of importance.

We have now developed methods that have enabled us to identify certain receptors to certain peptides of the bombesin family which enables them to be characterised. The bombesin family of peptides do have structural differences from one another but also have a common 7-amino acid sequence and we believe that the receptor we have identified is capable of acting as receptor to various members of the bombesin family, regardless of the species of origin of the bombesin-like peptide.

The receptor we have identified is a polypeptide having the following characteristics:

1. It is a single chain glycopolypeptide, having at least two mannose side chains.
2. It binds selectively with polypeptides of the bombesin type.
3. It has a molecular weight of 75 to 85 Kilodaltons (Kd).
4. It has an isoelectric point of 6.4 to 6.9.
5. Its core protein, obtained using endo-beta-N-glucosaminidase from *Flavobacterium meningosepticum*, has a molecular weight of about 42 Kd.
6. It binds with Antagonist A and Antagonist D, both as hereinafter defined.

Our invention provides, in one aspect, antagonists to the glycopolypeptide receptors as defined above. These antagonists are substances which are structurally quite different to bombesin and the bombesin-like peptides but which can bind to the bombesin receptor, and inhibit the effects of bombesin, but we believe, not by occupying binding sites that would otherwise be occupied by the bombesin-like peptides. Since bombesin-like peptides have been identified as present in high concentration in small cell lung carcinoma (18–21), and may act as autocrine growth factors (22), bombesin antagonists are of interest in providing a means of interfering with the receptor/bombesin peptide interaction and hence cell growth patterns influenced by the bombesin-like growth factor. We have now shown that an antagonist of bombesin that we have identified can inhibit the growth of human small cell lung cancer (SCLC) lines and is therefore of interest as a promising therapeutic entity.

So-called Substance P is an 11-mer neuropeptide, of interest in studies in pain transmission, which has the formula:

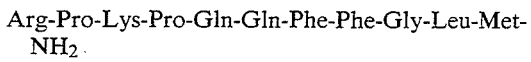

We have found that a commercially available structural variant of Substance P, known as [D-Arg[1], D-Pro[2], D-Trp[7,9], Leu[11]] Substance P and hence of the formula:

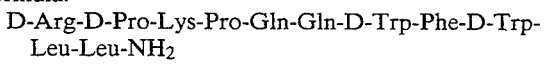

which we call Antagonist A and which is also known as [D-Pro[2]]spantide, is, surprisingly, able to act as a bombesin antagonist. Antagonist A is therefore of interest, according to the present invention, in the modification of cell growth influenced by the presence of bombesin-like peptides.

We have also found that a further commercially available structural variant of Substance P, which we call Antagonist D, which is also known as [D-Phe[5]]-spantide and which has the formula:

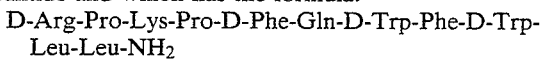

is even more potent as a bombesin antagonist than Antagonist A and hence is also of great interest for the modification of cell growth influenced by the presence of bombesin-like peptides.

Our studies of Antagonists A and D indicate to us the importance of structural variation at amino acid position 5 in compounds of this type to produce improved bombesin antagonists and the present invention extends to new compounds which are amino acid position 5 variants on Antagonist A and Antagonist D where the amino acid at position 5 is D-Trp, D-Tyr or Me-Phe and to such position 5-variants of Antagonist A and Antagonist D for use in method of treatment of the human or animal body by therapy or diagnosis of cancers where uncontrolled cell growth is associated with disorders of proteins of the bombesin family.

The antagonists of the invention may be formulated with pharmaceutically acceptable carriers or diluents e.g. conventional parenteral carriers so that the antagonists can be administered parenterally where they are of interest for use in a method of treatment of the human or animal body for diagnosis or therapy, of cancers where uncontrolled cell growth is associated with disorders of proteins of the bombesin family. The antagonists are also of interest for use in the production of a medicament for the treatment of uncontrolled cell proliferation.

The antagonists of the invention are also of interest for use in the in vitro diagnosis of uncontrolled cell proliferation by a method which includes the step of bringing the antagonist into contact with a body sample from a host suspected of suffering from uncontrolled cell proliferation. The method is particularly useful in the diagnosis of cancers by histology or serum assay.

The isolation and molecular characterisation of the receptors requires a procedure for their identification and we have developed a system involving the use of certain bifunctional cross-linking reagents which have already been used to identify membrane receptors in other systems (23 to 28). We have used the cross-linking agent ethylene glycol bis(succinimidyl succinate) to link covalently $^{125}$I labelled gastrin releasing peptide ([125]I-

GRP) to a surface protein in Swiss 3T3 cells. This surface protein, when isolated from the Swiss 3T3 cells, displays the characteristics of a specific receptor for the peptides of the bombesin family. This protein was not present in other cell lines which do not exhibit receptor properties for the bombesin-like peptides.

More specifically, the polypeptide receptor can be isolated by a process which comprises incubating a culture of Swiss 3T3 cells in a culture medium including $^{125}$I labelled gastrin releasing peptide ($^{125}$I-GRP), further incubating the $^{125}$I-GRP treated Swiss 3T3 cells in the presence of a bifunctional crosslinking reagent and solubilising the resulting $^{125}$I-GRP/crosslinking reagent/polypeptide conjugate to release the polypeptide from the cell surface.

Swiss 3T3 cells are widely available for experimental use and are available from the American Type Culture Collection in Rockville, Md. U.S.A., under the Deposit No. ATCC-CCL92.

The following Examples are given to illustrate the present invention.

EXAMPLE 1

Materials and Methods

Materials

Bombesin and litorin were obtained from Sigma. GRP, the 14–27 amino acid fragment of GRP and [D-Arg$^1$, D-Pro$^2$, D-Trp$^{7,9}$, Leu$^{11}$] substance P were obtained from Bachem Fine Chemicals (Saffrom Walden, U.K.) and the 1–16 fragment of GRP and neuromedin B were from Peninsula Laboratories (San Carlos, Calif.). Highly purified platelet-derived growth factor (PDGF) was obtained from Bioprocessing. Ethylene glycol bis (succinimidylsuccinate) (EGS), disuccinimidyl suberate (DSS), dithio-bis (succinimidylpropionate) (DSP) and bis [2-(succinimidooxycarbomyloxy)ethyl] sulphone (BSCOES) were purchased from Pierce Chemical Co. $^{125}$I-GRP (2000 Ci/mmol; 1Ci=37 GBq) was obtained from the Radiochemical Centre (Amersham, U.K.) or was prepared by radiolabelling GRP with $^{125}$I using the soluble lactoperoxidase method (29, 30). The labelled peptide was separated from unreacted Na $^{125}$I as described (8). $^{125}$I-GRP exhibited mitogenic activity within a similar concentration range to that observed with the unlabelled peptide. All other reagents used were of the highest grade available.

Chemical cross-linking of $^{125}$I-GRP to receptors

Confluent and quiescent cultures of Swiss 3T3 cells were incubated at 15° C. in 1 ml of medium consisting of 0.14M NaCl 5 mM KCl, 0.01M Na$_2$HPO$_4$, 1.8 mM KH$_2$PO$_4$, 1.8 mM CaCl$_2$, 1 mM MgCl$_2$, 25 mM 4-(2-hydroxyethyl)-1-piperazine ethane sulphonic acid (binding medium) pH 7.0, supplemented with 0.1% BSA and the appropriate concentration of $^{125}$I-GRP in the presence of absence of a 500-fold excess of unlabelled GRP. After 2.5 h the cells were washed three times at 15° C. with phosphate buffered saline (PBS) and then incubated for 15 min at 15° C. in 1 ml of binding medium, pH 7.4 in the presence of the appropriate cross-linking agent at the concentration indicated. The cross-linking agents (EGS, DSS, DSP and BSCOES) were dissolved in dimethyl sulphoxide immediately prior to use and were added to medium to give a final concentration of dimethylsulphoxide of 1–2%. The cultures were rapidly rinsed twice with PBS at 4° C. and solubilized in 0.1 ml of 2× sample buffer 0.2M Tris-HCl, pH 6.8, 10% (w/v) glycerol, 6% sodium dodecyl sulphate (SDS) (w/v) 4% β-mercaptoethanol (v/v) and 2 mM ethylenediaminetetraacetic acid. Samples were immediately heated at 100° C. for 3–5 min and analysed by either one or two-dimensional gel electrophoresis.

SDS-polyacrylamide gel electrophoresis

Slab gel electrophoresis was performed using 7.5% acrylamide in the separating gel and 5% in the stacking gel, and 0.1% SDS (31). After electrophoresis gels were stained, destained and dried down onto paper for autoradiography with Fuji X-ray film (Fuji Photo Film Co. Ltd. Japan). Dried gels were exposed to film for 4–8 days. Two-dimensional gel electrophoresis was performed as described by O'Farrell (32) using isoelectric focusing in the 1st dimension and SDS-polyacrylamide gel electrophoresis (SDS-PAGE) (8% polyacrylamide) in the second dimension. The samples prepared for isoelectric focusing containing 1.4% LKB ampholytes, pH 5–7, plus 0.6% LKD ampholytes, pH,3.5–10, 6M urea, and 2% Nonidet P-40. The Mr 75000–85000 band from autoradiograms was scanned using a Joyce-Loebl double beam densitometer and the areas under specific peaks were measured with a Hewlett-Packard digitizer.

Cell culture procedure (33), assays of DNA synthesis by $^3$H-thymidine incorporation (34) and $^{125}$I-GRP binding to intact cells (13) were performed as described previously.

Results and Discussion

Figure 1B:
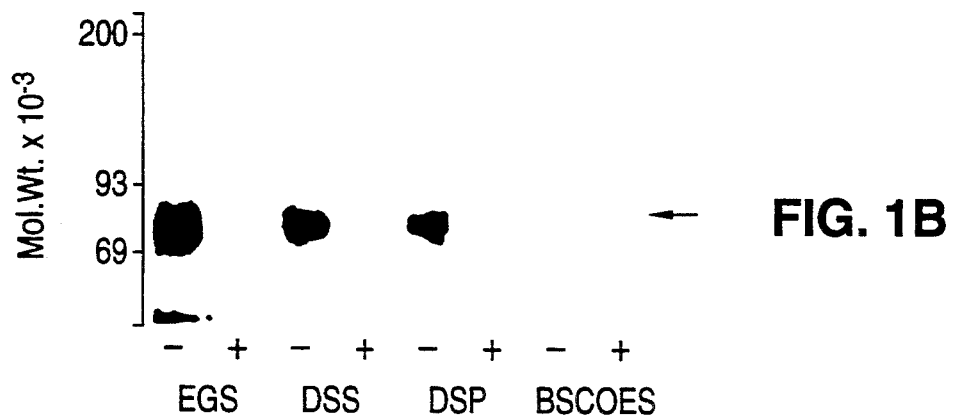
Figure 1C:
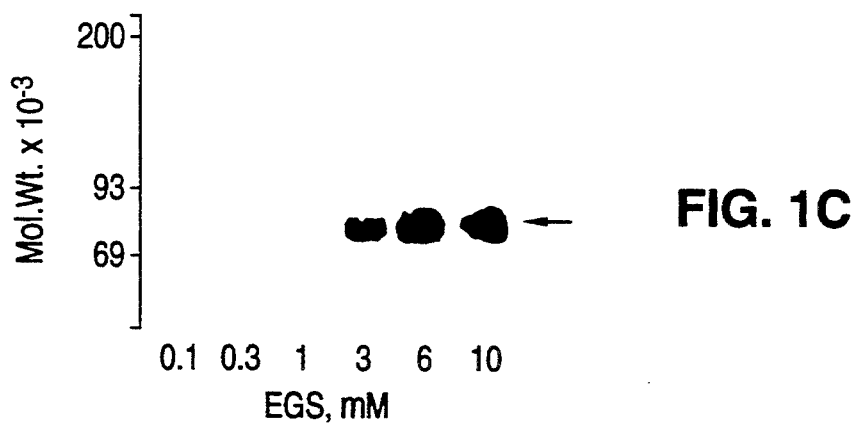

When cultures of confluent and quiescent Swiss 3T3 cells were incubated with $^{125}$I-GRP at 15° C. cell-associated radioactivity reached a maximum after 2.5 h (FIG. 1A) and was considerably enhanced compared with surface binding at either 37° C. or 4° C. (unpublished observations). Analysis by SDS-PAGE of cells which were incubated with 5 nM $^{125}$I-GRP at 15° C. for 2.5 h, and treated with the homobifunctional cross-linking agents EGS, DSS, DSP or BSCOES revealed the presence of a single major band of Mr 75000–85000 (FIG. 1B). Identical results were obtained using either commercially available $^{125}$I-GRP or GRP radiolabelled with $^{125}$I in our laboratory. In the presence of 500-fold excess unlabelled GRP(+) this band was completely abolished. EGS displayed the greatest efficiency of cross-linking and this agent was therefore used in subsequent experiments. The effect of EGS on the level of the Mr 75000–85000 protein was concentration-dependent; the half-maximal effect of EGS was obtained at a concentration of 2 mM (FIGS. 1C). The rank order of cross-linking efficiency (EGS>DSS>DSP>BSCOES) may be related to the chain length of the arms of these bifunctional molecules. Thus BSCOES which has the shortest chain length was virtually ineffective (FIG. 1B). The Mr 75000–85000 protein appeared as a multicomponent spot migrating with an isoelectric point of 6.4 to 6.9 when cross-linked cultures of Swiss 3T3 cells were analysed by two-dimensional gel electrophoresis using isoelectric focusing in the first dimension and SDS-PAGE in the second dimension (results not shown).

The Mr 75000–85000 band was not obtained when the cross-linking reaction was carried out either in the absence of the cross-linking agent, in plastic dishes without cells, or using other cell lines including Rat-1, whole mouse embryo fibroblasts and Balbc/3T3, which neither exhibit significant specific $^{125}$I-GRP binding, nor respond mitogenically to bombesin-related peptides (13). The possibility that the affinity labelled band was a degradation product of a higher molecular weight protein was tested by extracting cultures after the cross-linking reaction in the presence of the protease inhibitors aprotinin (100 μg/ml), pepstatin (4 μg/ml), phenylmethylsulphonylfluoride (2 mM) and ethyleneglycol-bis-(β-aminoethyl ether)N,N'-tetra-acetic acid (4 mM). These treatments had no significant effect on the level of the Mr 75000–85000 protein and did not result in the appearance of any higher molecular weight proteins. In another experiment performed at 4° C. to prevent ligand internalization and degradation identical results were obtained to those shown in FIG. 1 (results not shown). Thus, the Mr 75000–85000 protein was neither an intracellular component associated with internalized $^{125}$I-GRP or a product of peptide degradation, nor a fragment arising from proteolysis of a larger molecule. In addition, treatment with 0.6 M 2-mercaptoethanol did not result in the appearance of additional bands of lower molecular weight suggesting that the Mr 75000–85000 protein consists of a single polypeptide chain. These important controls strongly suggested that the Mr 75000–85000 band was a surface component of Swiss 3T3 cells closely related to the receptor for peptides of the bombesin family.

Figure 2A:
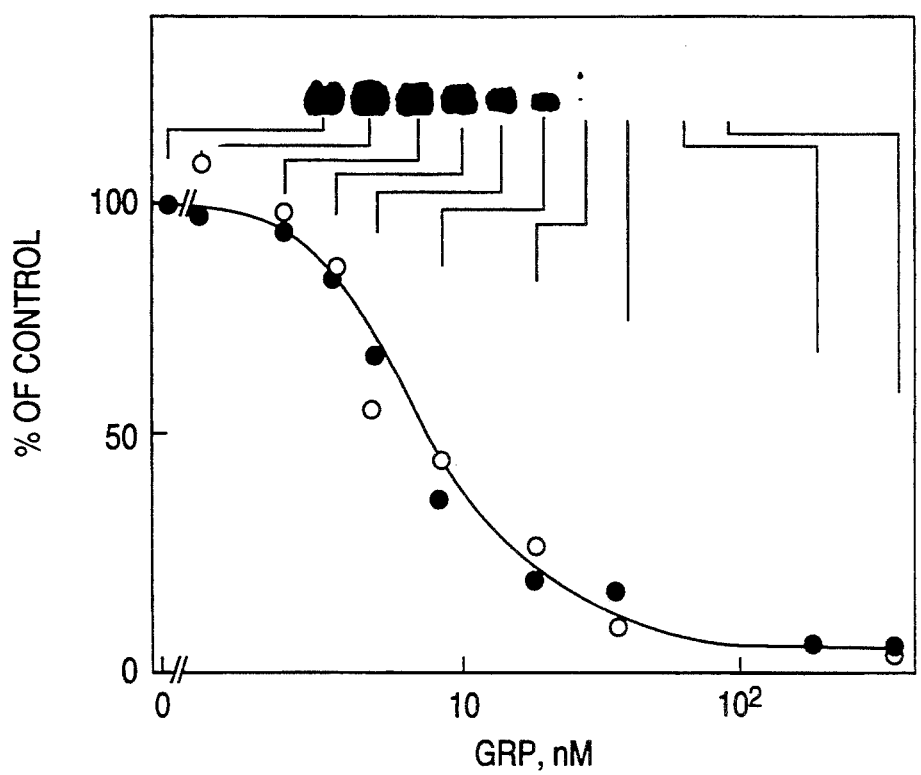

The above conclusion was further substantiated by cross-linking $^{125}$I-GRP to cultures incubated in the presence of different concentrations of unlabelled peptide. The decrease in the level of the Mr 75000–85000 band with increasing concentrations of unlabelled GRP (FIG. 2A, open symbols) closely paralleled the ability of GRP to inhibit the binding of an identical concentration of $^{125}$I-GRP in a parallel set of cultures (FIG. 2A, closed symbols). The cross-linking of $^{125}$I-GRP to Swiss 3T3 cells was also markedly inhibited by other peptides structurally related to GRP including bombesin, neuromedin B, litorin and the bombesin antagonist [D-Arg$^1$, D-Pro$^2$, D-Trp$^{7,9}$, Leu$^{11}$] substance P (13,17,35,36). The amino-terminal fragment of GRP (GRP(1–16)) which neither inhibits $^{125}$I-GRP binding, nor stimulates DNA synthesis (13) caused no reduction in the level of the Mr 75000–85000 protein (Table 1). To ascertain the specificity with which $^{125}$I-GRP recognizes the Mr 75000–85000 protein, Swiss 3T3 cells were incubated with $^{125}$I-GRP in the presence of a variety of other mitogens for these cells. As shown in Table 1, the level of the protein obtained by treatment with EGS was not substantially affected by saturating concentrations of PDGF, epidermal growth factor (EGF), vasopressin, insulin, and phorbol 12,13-dibutyrate (1,37,38). In addition the neuropeptides substance P, substance K and somatostatin also had no effect on affinity labelling of the Mr 75000–85000 band (Table 1). This result is in accord with the finding that the binding of $^{125}$I-GRP to intact 3T3 cells is also not inhibited by these mitogens (13).

Figure 2B:
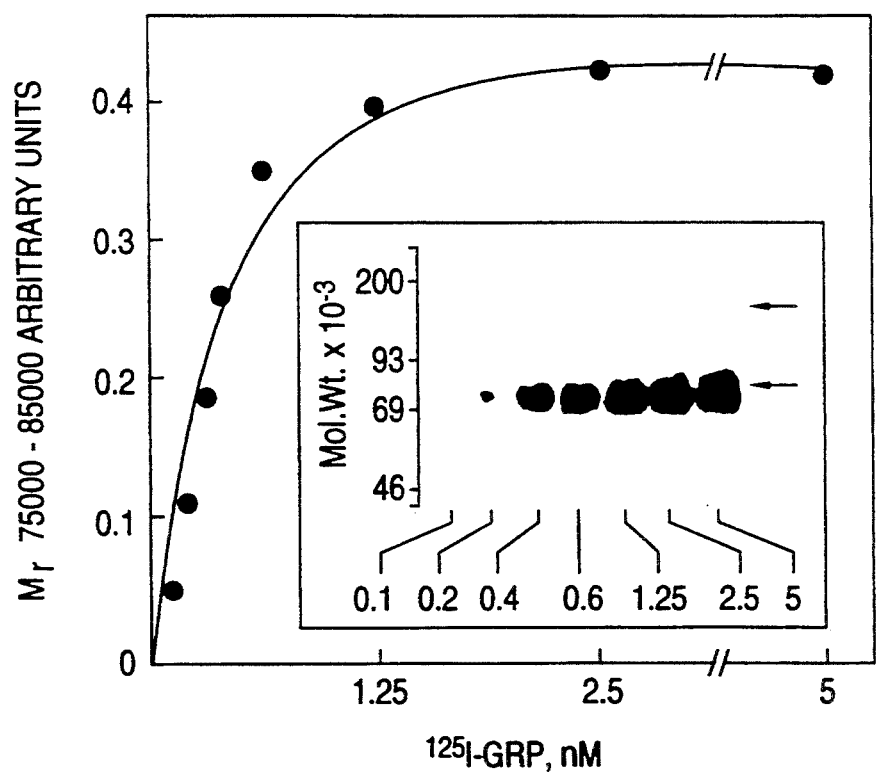

The conclusion that the Mr 75000–85000 protein is a major component of the receptor for peptides of the bombesin family in Swiss 3T3 cells was further strengthened by measuring the level of the protein as a function of the concentration of the radioiodinated ligand. FIG. 2B shows that the cross-linking of $^{125}$I-GRP to the Mr 75000–85000 band increased in a saturable manner with increasing concentration of the labelled peptide. A double-reciprocal plot of these data (not shown) produced a straight line and gave a value for the Kd of 1 nM which compares very favourably with the Kd ($0.5 \times 10^{-9}$M) obtained from Scatchard analysis of binding curves (13). Furthermore, the dependence of affinity labelling of the Mr 75000–85000 protein on $^{125}$I-GRP concentration closely parallels the ability of the peptide to stimulate a variety of early biological responses (16,17) and DNA synthesis (13) in quiescent Swiss 3T3 cells. At high concentrations of $^{125}$I-GRP a higher molecular weight band of approximately Mr 160,000 was observed (FIG. 2B). This band represented 4% of the total cross-linked material and was almost undetectable either at lower levels of $^{125}$I-GRP or at 4° C.

Footnote[1] The abbreviations used are: GRP, gastrin releasing peptide; BSA, bovine serum albumin; PBS, phosphate-buffered saline; EGF, epidermal growth factor; PDGF, platelet-derived growth factor; EGS, ethyleneglycolbis (succinimidylsuccinate); DSS, disuccinimidyl suberate; DSP, dithio-bis-(succinimidylpropionate); BSCOES, bis[2-(succimidooxycarbomyloxy)ethyl]sulphone; SDS-PAGE, sodium dodecyl sulphate-polyacrylamide gel electrophoresis.

EXAMPLE 2

This illustrates the more than Fivefold potency of Antagonist D over Antagonist A.

[DPhe$^5$]spantide is a potent inhibitor of GRP-mediated mitogenesis

Substance P has a slight amino acid sequence homology with bombesin (Table 2) and neither inhibits the binding of GRP to Swiss 3T3 cells nor stimulates DNA synthesis. However, [DPro$^2$]spantide (Antagonist A, Table 2) which was synthesized as a substance P antagonist was found to be a bombesin antagonist in pancreatic acinar cells and to block the growth-promoting effects of bombesin in Swiss 3T3 cells. In order to identify a more potent antagonist of bombesin-like peptides, we have tested ten substance P antagonists at 50 μM (Table 2) for their ability to inhibit mitogenesis stimulated by GRP (the mammalian homologue of bombesin in Swiss 3T3 cells. [DPhe$^5$]spantide (Antagonist D) was clearly the most potent GRP antagonist. In contrast, peptides, B, C, E, F, G, H, J and K were less potent than either A or D. Spantide (B) had no antagonist activity even at 100 μM. None of the peptides stimulated DNA synthesis when tested at 20 μM with insulin at 1 μg/ml i.e. none exhibited any agonist activity.

Figure 3A:
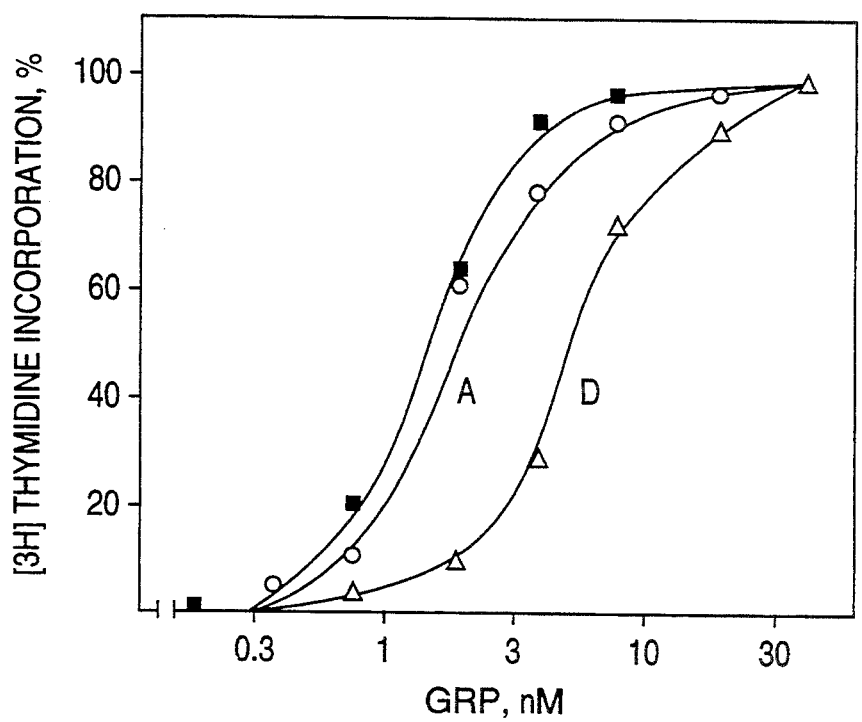
Figure 3B:
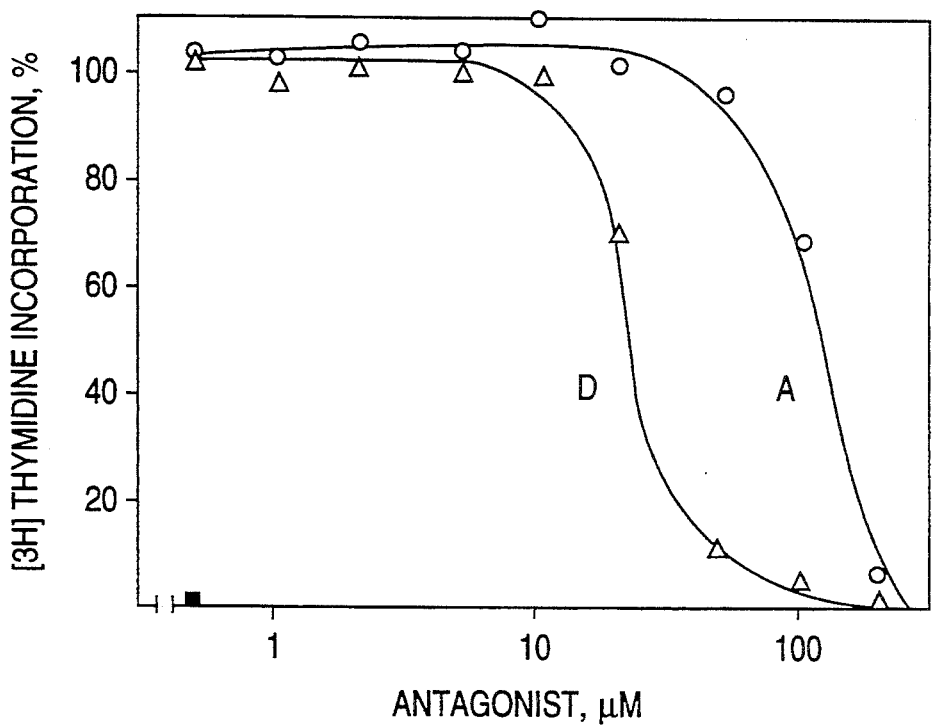

Following the identification of [DPhe$^5$]spantide as the most promising GRP antagonist, we compared the potency of [DPhe$^5$]spantide with that of [DPro$^2$]spantide. FIG. 3 shows that [DPhe$^5$]spantide at 20 λM markedly increased the concentration of GRP required to produce half-maximal stimulation of DNA synthesis whereas addition of [DPro$^2$]spantide also at 20 λM had only a slight effect. Inhibition of DNA synthesis by [DPhe$^5$]spantide was completely reversed by high concentrations of GRP, indicating that its inhibitory effect was competitive and reversible. The dose response curves for the two antagonists in the presence of GRP 3.6 nM are shown in FIG. 3 (right). Half-maximal inhibition of DNA synthesis was obtained with 22 μM [DPhe$^5$]spantide and 118 μM [DPro$^2$]spantide. Thus, [DPhe$^5$]spantide is 5.4-fold more potent than [DPro$^2$]spantide in inhibiting DNA synthesis induced by GRP.

The following Examples demonstrate that Antagonist D inhibits all of the events initiated by Bombesin/GRP in a specific manner.

EXAMPLE 3

[DPhe⁵]spantide binds competitively to the GRP receptor

Figure 4A:
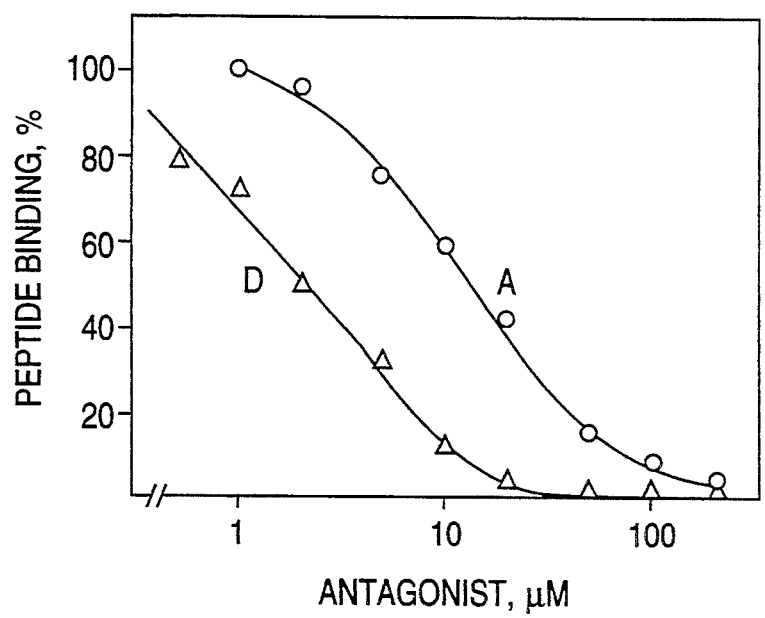
Figure 4B:
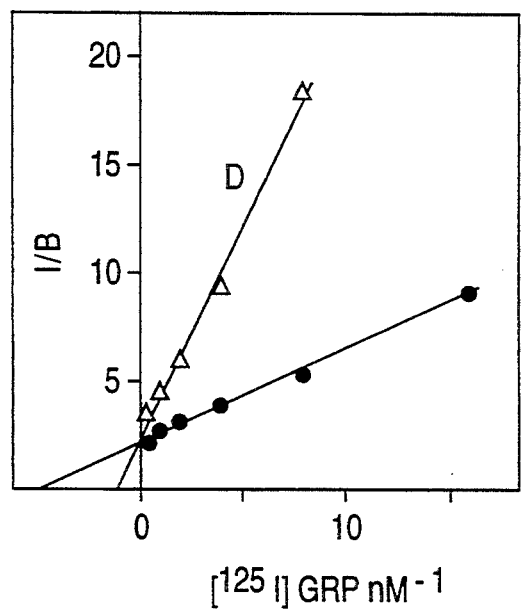
Figure 4C:
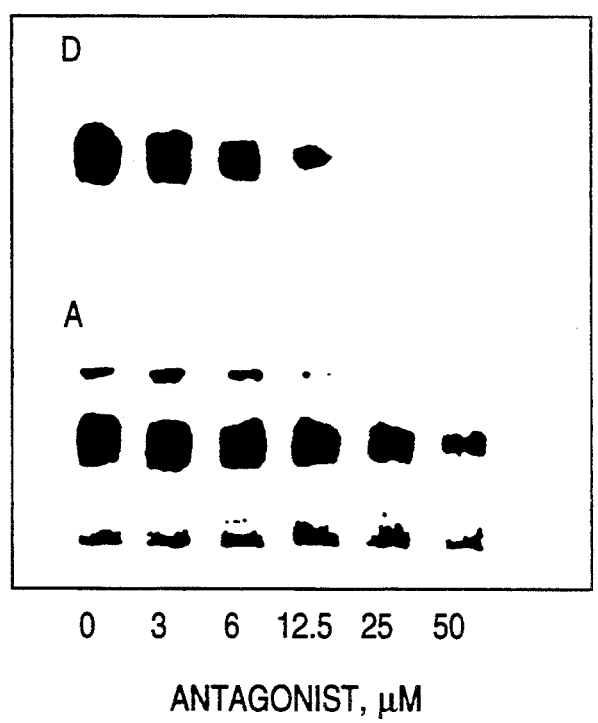

The preceding results demonstrate that [DPhe⁵]spantide is a potent inhibitor of GRP-induced DNA synthesis which exhibits specificity against other mitogens. To elucidate its mechanism of action, we examined the effect of [DPhe⁵]spantide on the specific binding of [$^{125}$I]GRP to Swiss 3T3 cells. FIG. 4 (left) shows that both [DPro²]spantide and [DPhe⁵]spantide caused a concentration-dependent inhibition in the specific binding of [$^{125}$I]GRP (1 nM). Half-maximal inhibition of binding was achieved with 2.3 μM of [DPhe⁵]spantide and 14 μM of [DPro²]spantide, a 6.1-fold difference in potency. This is consistent with the relative potencies of the two antagonists in inhibiting DNA synthesis induced by GRP.

The binding of different concentrations of [$^{125}$I]GRP was measured in the absence and presence of 10 μM [DPhe⁵]spantide. A double reciprocal plot of these data (FIG. 4, center) shows that [DPhe⁵]spantide markedly reduces the affinity of the receptors of [$^{125}$I]GRP, although the number of binding sites is unchanged. This is consistent with results previously obtained with [DPro²]spantide and strongly suggests that these peptides bind competitively to the GRP receptor.

To further substantiate these findings, we investigated the effects of the two antagonists on the affinity-labelling of the recently described Mr 75000–85000 protein which is a putative bombesin receptor (FIG. 4, right). They were both able to differentially inhibit the Mr 75000–85000 protein obtained by cross-linking [$^{125}$I]GRP to Swiss 3T3 cells with EGS. Half-maximal inhibition (obtained by scanning densitometry of the autoradiographs) was achieved with [DPhe⁵]spantide at 5.5 μM and [DPro²]spantide at 20 μM, again demonstrating the superiority of [DPhe⁵]spantide.

EXAMPLE 4

[DPhe⁵]spantide inhibits the early events elicited by GRP

Figure 5B:
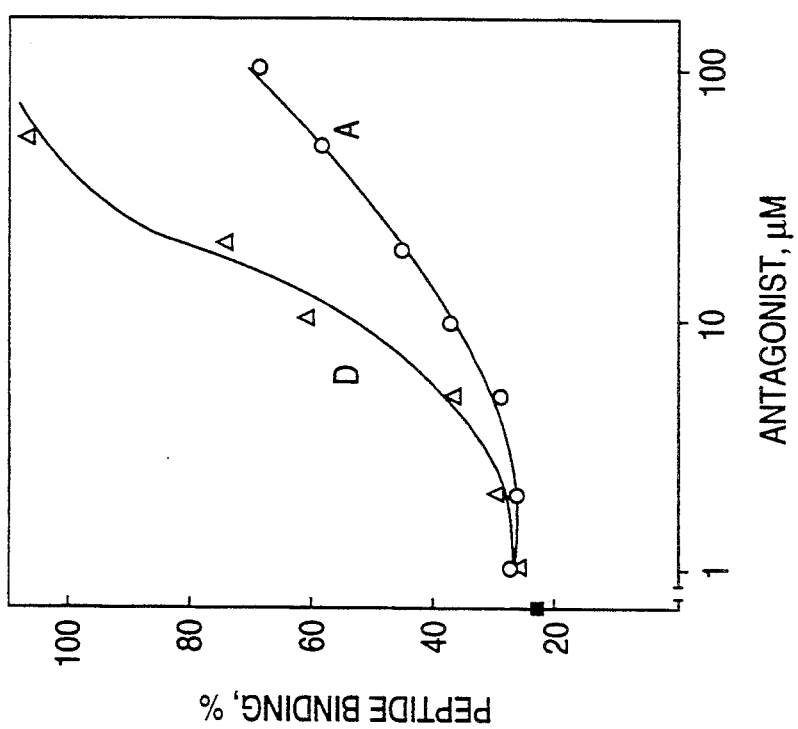
Figure 5A:
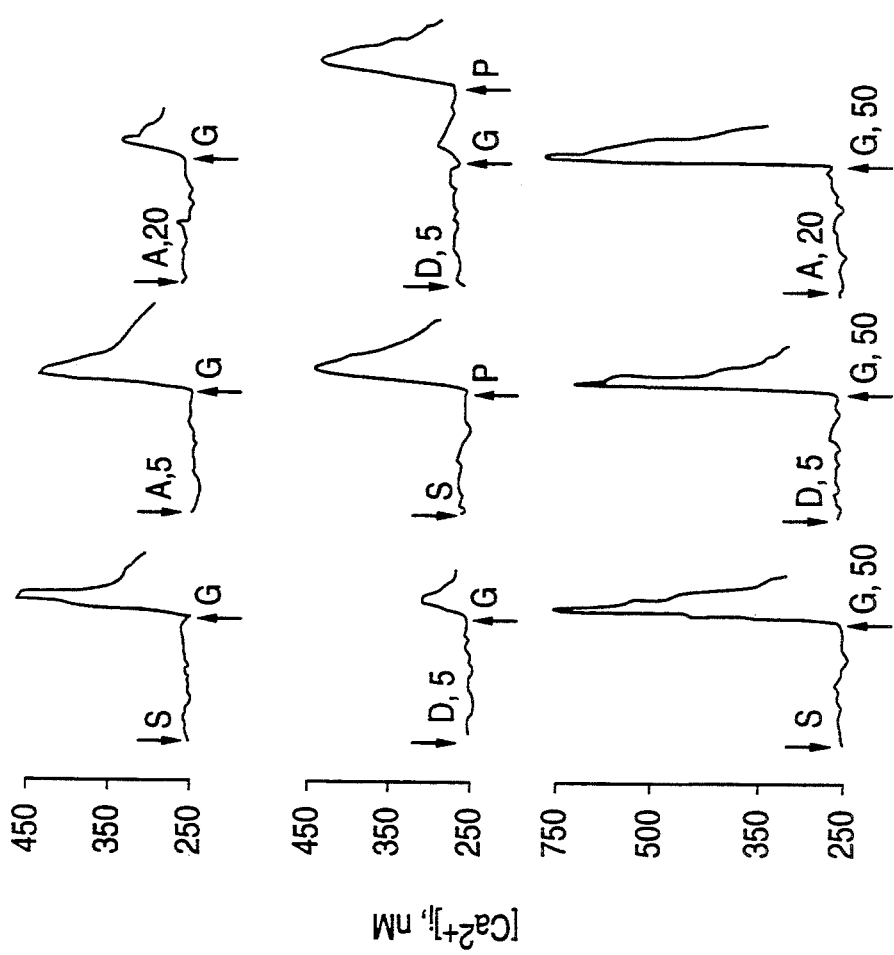

One of the earliest events stimulated by addition of bombesin or GRP to quiescent Swiss 3T3 cells is an increase in cytosolic Ca$^{2+}$ concentration ([Ca$^{2+}$]$_i$). FIG. 5 (left) shows that the rise in [Ca$^{2+}$]$_i$ caused by the addition of GRP (1 nM) to quiescent Swiss 3T3 cells was prevented by the addition of [DPro²]spantide at 20 μM but not at 5 μM. In contrast [DPhe⁵]spantide was effective at 5 μM, demonstrating that [DPhe⁵]spantide is at least 4-fold more potent than [DPro²]spantide in this assay. These effects were specific and reversible since [DPhe⁵]spantide at 5 μM did not prevent a response to PDGF and because the effects of the antagonist in preventing Ca$^{2+}$ mobilization in response to 5 nM GRP was reversed by addition of GRP at 50 nM.

Inhibition of [$^{125}$I]EGF binding by GRP, which is mediated by the protein kinase C pathway, was reversed in a concentration-dependent fashion by [DPro²]spantide and [DPhe⁵]spantide (FIG. 5, right). Half-maximal reversal of inhibition was obtained with [DPhe⁵]spantide at 8.7 μM and [DPro²]spantide at 30 μM. These findings further substantiate the conclusion that [DPhe⁵]spantide is a potent GRP antagonist.

EXAMPLE 5

In addition to the demonstration of inhibition of the cellular effects of Bombesin/GRP in mouse 3T3 cells we have now shown that Antagonists A and C can inhibit the growth of SCLc cells in a specific and reversible fashion.

SCLC is known to secrete bombesin-like peptides which have been suggested to act as autocrine growth factors. Thus it is plausible but as yet unproven that an antagonist to bombesin/GRP will inhibit SCLC growth, so we have now tested the effects of [DPro²]spantide and [DPhe⁵]spantide on SCLC in vitro.

Figure 6A:
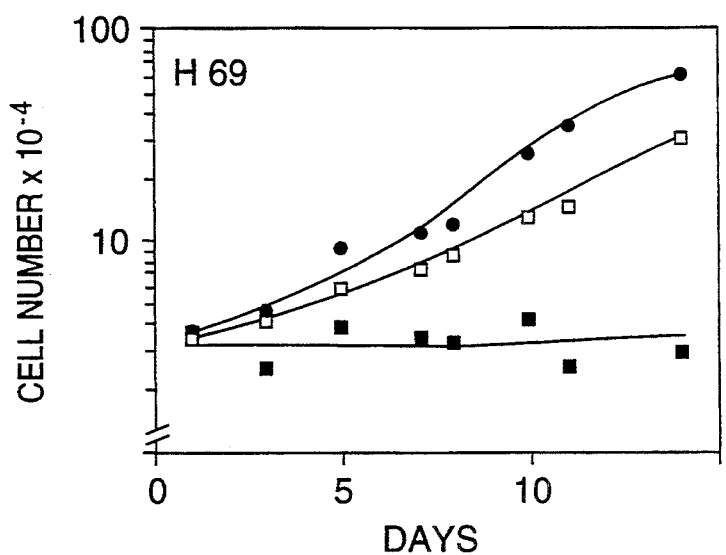
Figure 6B:
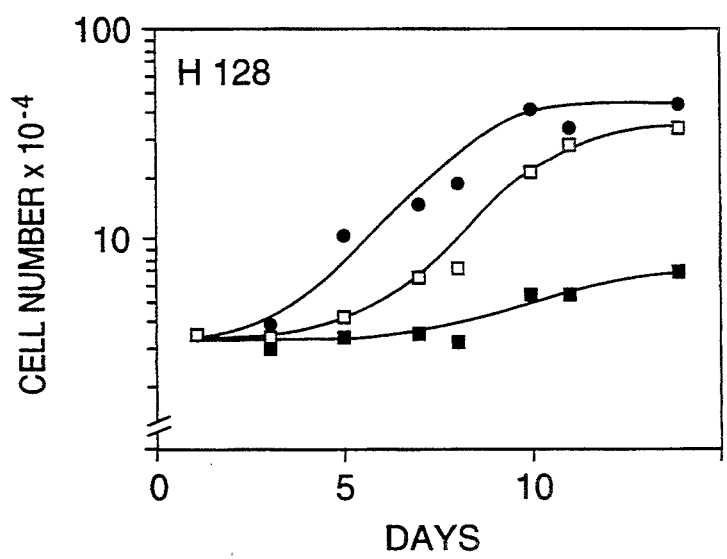
Figure 6C:
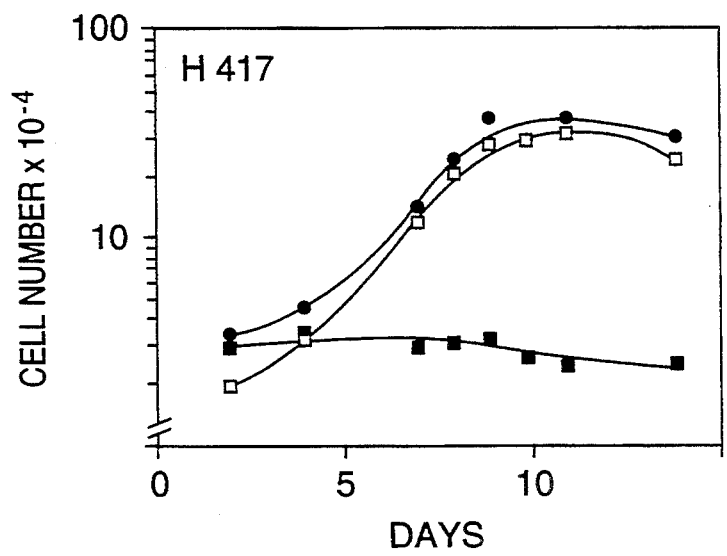

FIG. 6 shows that the rate of growth of the SCLC lines H69, H128 and H417 in serum-free medium was abolished by addition of [DPro²]spantide at 150 μM, a concentration that reversibly inhibits GRP-induced mitogenesis in Swiss 3T3 cells. The inhibition of growth by the antagonist in SCLC cell lines was reversed by washing the cells and resuspending them in serum-free medium.

Figure 7A:
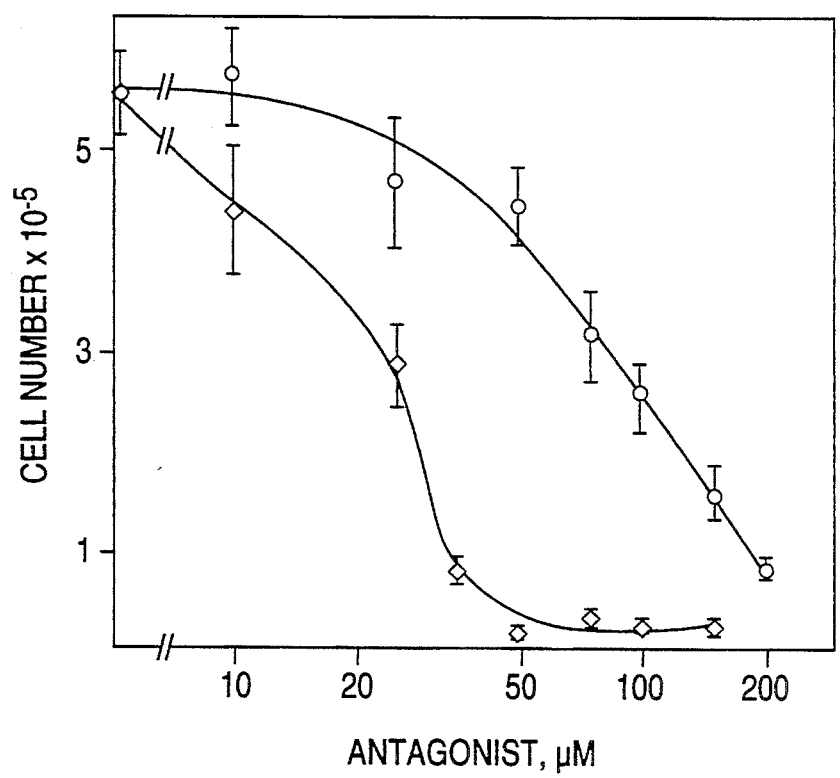
Figure 7B:
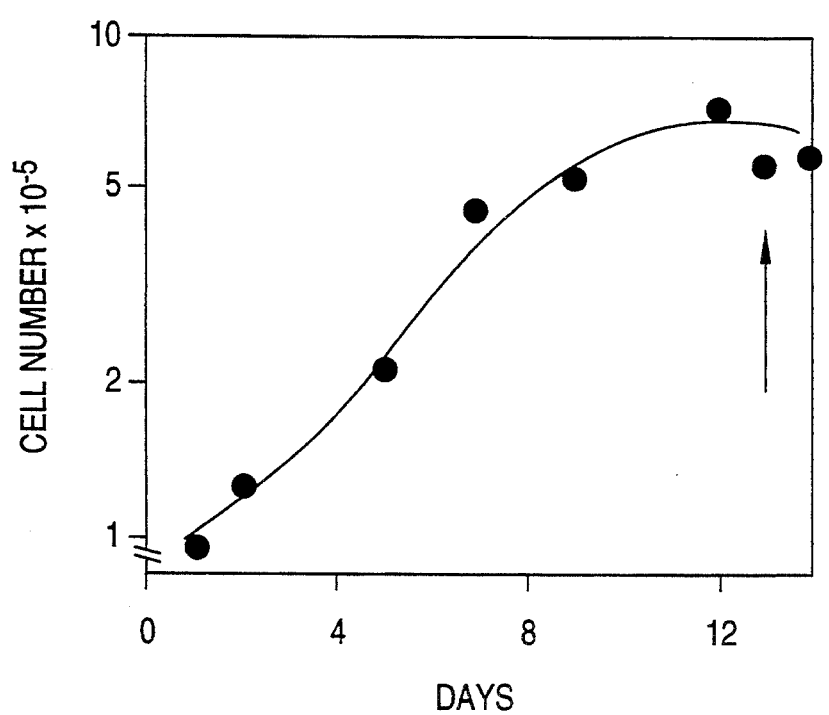

The effects of [DPro²]spantide and [DPhe⁵]spantide on H69 cells are compared in FIG. 7. The cells achieve 10-fold increase in number in about 12 days in serum-free medium (inset). Both antagonists inhibited growth in a dose-dependent manner; half-maximal effect was seen at 24 μM and [DPhe⁵]spantide and at 82 μM with [DPro²]spantide. The difference in potency is of the same magnitude as that demonstrated in Swiss 3T3 cells and supports the contention that bombesin-like peptides (or vasopressin) may be important growth factors for SCLC.

Figure Legends

FIG. 1: A. Time-dependence of $^{125}$I-GRP binding to Swiss 3T3 cells at 15° C. Cultures were washed and then incubated at 15° C. in 1 ml binding medium containing $^{125}$I-GRP (2 nM). After various times the cells were rapidly washed four times with cold (4° C.) PBS supplemented with 1 mg/ml bovine serum albumin (BSA) and then incubated with 1 ml 0.2M acetic acid, 0.5M NaCl at 4° C. for 6 min to remove cell-surface associated ligand. This medium was then removed for counting and the remaining intracellular cell-associated radioactivity extracted with 1 ml 0.1M NaOH containing 2% Na$_2$CO$_3$ and 1% SDS. Open squares denote surface bound ligand and closed squares intracellular radioactivity. B. $^{125}$I-GRP affinity labelling of an Mr 75000–85000 cellular protein using dissuccinimidyl cross-linking agents. Confluent cultures of Swiss 3T3 cells were washed and then incubated with $^{125}$I-GRP (5 nM) in the presence (+) or absence (−) of 0.9 μM unlabelled GRP for 2.5 h at 15° C. The cells were then rinsed to remove free ligand and treated with either EGS, DSS, DSP or BSCOES at concentrations of 6 mM, 2 mM, 2 mM and 4 mM respectively. The cells were solubilized in SDS sample buffer and electrophoresed on a 7.5% polyacrylamide gel. The arrow indicates the position of the Mr 75000–85000 protein. All other experimental procedures used in this and similar experiments were as described in Materials and Methods. A broad and intensely radioactive band migrating at low molecular weight was observed in all our gels. This material was not obtained in the presence of excess unlabelled GRP and therefore is most likely to represent the unreacted peptide. C. Concentration-dependence of the effect of EGS on the affinity-labelling of the Mr 75000–85000 protein. Confluent cultures of Swiss 3T3 cells were incubated with 1 nM $^{125}$I-GRP at 15° C. and then treated with various concentrations of EGS as indicated. Samples were prepared for SDS PAGE as described in Materials and Methods. The arrow indicates the position of the Mr 75000–85000 protein. In this and other experiments the efficiency of cross-linking using EGS ranged from 5 to 10% of cell-surface associated radioactivity.

FIG. 2: A. Effect of varying concentrations of unlabelled GRP on the $^{125}$I-GRP binding to intact Swiss 3T3 cells (●) and the affinity labelling of the Mr 75000–85000 protein (○). Confluent cultures of 3T3 cells were incubated with 5 nM $^{125}$I-GRP in the presence of varying concentrations of non-radioactive ligand at 15° C. for 2.5 h. After this time some cells were washed four times with cold (4° C.) PBS supplemented with 1 mg/ml BSA, solubilized and total cell associated radioactivity was then determined in a gamma counter. Parallel cultures were rinsed with PBS at 15° C. and then treated with EGS (6 mM) to cross-link bound $^{125}$I-GRP. The cells were then solubilized and samples were analyzed by SDS-PAGE. After electrophoresis, gels were dried, exposed to film and scanned as described in Materials and Methods. The areas under the individual peaks for the Mr 75000–85000 protein are shown as a function of the concentration of the unlabelled peptide and are expressed as a percentage of the control. The inset shows the region of the autoradiogram used for the scanning. B. Concentration-dependence of $^{125}$I-GRP affinity labelling of the Mr 75000–85000 protein. Confluent cultures of Swiss 3T3 cells were incubated with different concentrations of $^{125}$I-GRP at 15° C. for 2.5 h, and treated with EGS (6 mM). The level of the Mr 75000–85000 protein expressed in arbitrary units is shown as a function of the concentration of the labelled ligand. Inset: autoradiogram of the gel used for scanning; the Mr 75000–85000 and 160,000 bands are indicated by arrows. All other experimental details were as described in Materials and Methods.

FIG. 3. Inhibition of GRP-induced DNA synthesis by [DPro$^2$]spantide (A) and [DPhe$^5$]spantide (D). Left: Confluent and quiescent cultures of Swiss 3T3 cells in 35 mm plastic dishes were washed twice with DMEM then incubated at 37° C. in 2 ml of a 1:1 mixture of DMEM/Waymouth medium containing [$^3$H]thymidine at 1 μCi/ml (1 μM), insulin at 1 μg/ml and increasing concentrations of GRP in the absence (■) or presence of antagonist A at 20 μM (○) or antagonist D at 20 μM (Δ). After 40 hours DNA synthesis was estimated by [$^3$H]thymidine incorporation into acid-precipitable material. Values are expressed as a percentage of [$^3$H]thymidine-incorporation obtained with a saturating level of GRP (36 nM) in the absence of antagonist (100%=8.4×10$^5$ cpm per dish). Each point represents the mean of duplicate determinations. Right: Cultures of Swiss 3T3 cells were washed and incubated as above, except that the concentration of GRP was fixed at 3.6 nM with various concentrations of antagonists A (○) and D (Δ). Values are expressed as a percentage of [$^3$H]thymidine incorporation obtained in the absence of antagonists (100%=8.6×10$^5$ cpm per dish). Each point represents the mean of 4 determinations.

FIG. 4. Effects of [DPro$^2$]spantide (A) and [DPhe$^5$]-spantide (D) on the binding of $^{125}$I-labelled GRP ([$^{125}$I]GRP) to Swiss 3T3 cells. Left: Inhibition of specific [$^{125}$I]GRP binding by antagonists A and D. Confluent and quiescent cells were washed twice with DMEM then incubated at 37° C. in 1 ml of binding medium (3) containing [$^{125}$I]GRP at 1 nM and various concentrations of antagonist A (○) and D (Δ). Cell-associated [$^{125}$I]GRP binding was measured after 30 minutes. Values are expressed as percentage of the specific binding obtained in the absence of antagonists. Non-specific binding was determined by the addition of 300-fold excess of unlabelled GRP. Each point represents the mean of 3 determinations. Center: Effect of antagonist D on the affinity of binding sites in Swiss 3T3 cells for [$^{125}$I]GRP. Confluent and quiescent cells were washed twice with DMEM then incubated for 30 minutes at 37° C. in 1 ml of binding medium containing various concentrations of [$^{125}$I]GRP in the absence (●) or presence (Δ) of D at 10 μM. Specific binding (B) is expressed in pmol/10$^6$ cells and is shown in a double-reciprocal plot. Each point represents the mean of duplicate determinations. Right: Effects of antagonists A and D on the affinity labelling of the bombesin receptor-associated Mr 75000–85000 protein. Confluent cultures of Swiss 3T3 cells were washed twice with DMEM and incubated at 15° C. in 1 ml of binding medium (pH 7.0) (15) containing 0.5 nM [$^{125}$I]GRP and various concentrations of the antagonists. After 2 hours, the cultures were washed twice with binding medium then incubated in 1 ml containing 6 mM ethylene glycol bis (succinimidylsuccinate) (EGS) at pH 7.4 for 15 minutes at 15° C. The cultures were then washed twice with cold phosphate-buffered saline and solubilised in 0.1 ml of 2× sample buffer, then immediately heated at 100° C. for 5 minutes and electrophoresed on a 10% polyacrylamide gel.

FIG. 5. Effects of [DPro$^2$]spantide (A) and [DPhe$^5$-spantide (D) on the early cellular responses stimulated by GRP. Left: Effects of antagonists on [Ca$^{2+}$]$_i$. Quiescent Swiss 3T3 cells grown on Cytodex 2 beads were washed twice with DMEM and incubated for 10 minutes with fura-2 tetracetoxymethyl ester at 1 μM, then washed three times and suspended in 2 ml of electrolyte solution (6) in the fluorimeter at 37° C. and stirred. Fluorescence was recorded continuously in a Perkins-Elmer LS5 luminescence spectrometer with an excitation wavelength of 335 nM and emission wavelength of 510 nM. After a period of equilibration, the following additions were made: solvent, S; antagonist A at 5 μM, A, 5 and 20 μM, A, 20; antagonist D at 5 μM, D, 5. After 3 minutes in each case, GRP was added at 1 nM, G or at 50 nM, G, 50; PDGF at 1 nM, P. Right: Antagonists A and D reverse the inhibition of [$^{125}$I]EGF binding induced by GRP. Confluent and quiescent cultures of Swiss 3T3 cells were washed twice with DMEM then incubated for 1 hour at 37° C. in 1 ml of binding medium (9) containing [$^{125}$I]EGF at 0.2 nM and GRP at 3.6 nM alone (■) or in the presence of various concentrations of A (○) or D (Δ). Values are expressed as percentages of the specific binding obtained with [$^{125}$I]EGF alone at 0.2 nM. The non-specific binding was obtained by the addition of 500-fold excess of unlabelled EGF. Each point represents the mean of 6 determinations.

FIG. 6. [DPro$^2$]spantide reversibly inhibits the growth of SCLC cell lines. Stock cultures of cell lines H69, H128 and H417 were maintained in RPMI 1640 medium with 10% fetal bovine serum (heat inactivated) in a humidified atmosphere of 10%-CO$_2$:90% air at 37° C. They were passaged every 7 days. Identical growth was obtained in the serum-free medium of RPMI 1640 supplemented with HITES (29) (hydrocortisone, 10 nM; insulin, 5 μg/ml; transferrin, 100 μg/ml; 17β-estradiol, 10 nM; sodium selenite, 30 nM) and 0.25% bovine serum albumin. Cells were washed twice with RPMI 1640 medium then incubated in the serum-free medium in the absence (•) or presence (□,■) of [DPro²]spantide at 150 μM. After 4 days they were again washed twice with RPMI 1640 medium then resuspended at a density of 5×10⁴ cells per ml in the absence (•,□) or presence (■) of [DPro²]spantide at 150 μM (Day 0). Cell number was determined at intervals over 14 days in a Coulter Counter after disaggregation of cell clumps by syringing through 19 G and 21 G needles. Each point represents the mean of 3 determinations.

FIG. 7. Inhibition of SCLC growth in vitro by [DPro²]spantide and [DPhe⁵]spantide is concentration-dependent. Cultures of H69 cells were washed twice with RPMI 1640 medium then incubated in serum-free medium (as in FIG. 6) in the absence (•) or presence of various concentrations of [DPro²]spantide (○,▲) and [DPhe⁵]spantide (△,D). Cell number was determined in a Coulter Counter after disaggregation of cell clumps by syringing through 19 G and 21 G needles. Samples were incubated for 13 days, when the controls (inset) had achieved 10-fold increase in number, indicated by the arrow. Each point represents the mean (±standard deviation) of 5 determinations.

Table 1
Specificity of $^{125}$I-GRP affinity labelling of the $M_r$ 75000-85000 protein

| Addition | $M_r$ 75000-85000 protein % of control |
| --- | --- |
| — | 100 |
| GRP | 0.8 |
| GRP (14–27) | 0.4 |
| Bombesin | 0.5 |
| Litorin | 2 |
| Nouromedin B | 10 |
| [D-Arg¹,D-Pro²,D-Trp⁷,⁹,Leu¹¹] Substance P | 9.7 |
| GRP (1–16) | 93 |
| PDGF | 99 |
| EGF | 94 |
| Vasopressin | 94 |
| Insulin | 90 |
| Phorbol 12,13-dibutyrate | 99 |
| Substance P | 91 |
| Substance K | 94 |
| Somatostatin | 97 |
| Neurotensin | 93 |

Confluent cultures of Swiss 3T3 cells were incubated with $^{125}$I-GRP (0.5 nM) at 15° C. for 2.5 h in either the absence (−) or presence of the following GRP-related peptides at the concentrations indicated: GRP (360 nM), the 14–27 amino acid fragment of GRP (GRP (14–127)) (30 nM), bombesin (30 nM), litorin (92 nM), neuromedin B (220 nM), the bombesin antagonist [D-Arg¹,D-Pro², D-Trp⁷,⁹, Leu¹¹] substance P (100 nM) and the 1–16 amino acid fragment of GRP (GRP (1–16)) (3230 nM). Parallel cultures were incubated with the same concentration of $^{125}$I-GRP in the presence of the following unrelated factors: PDGF (5 nM), EGF (83 nM), vasopressin (1000 nM), insulin (1 μg/ml), phorbol 12,13 dibutyrate (2000 nM), substance P (740 nM), substance K (880 nM), somatostatin (610 nM) and neurotensin (600 nM). After the incubation period cultures were treated with 6 nM EGS as described in Materials and Methods. Each value is expressed as a percentage of the level of the $M_r$ 75000–85000 protein obtained with no additions (−). Other experimental details are as described in Materials and Methods.

TABLE 2

| Bombesin | pGlu—Gln—Arg—Leu—Gly—Asn—Gln—Trp—Ala—Val—Gly—His—Leu—Met—NH₂ |
| --- | --- |
| | 1    2    3    4    5    6    7    8    9    10    11 |
| Substance P | Arg—Pro—Lys—Pro—Gln—Gln—Phe—Phe—Gly—Leu—Met—NH₂ |
| Antagonist A | DArg—DPro—Lys—Pro—Gln—Gln—DTrp—Phe—DTrp—Leu—Leu—NH₂ |
| B | DArg—Pro—Lys—Pro—Gln—Gln—DTrp—Phe—DTrp—Leu—Leu—NH₂ |
| C | Arg—DPro—Lys—Pro—Gln—Gln—DPhe—Phe—DTrp—Leu—Met—NH₂ |
| D | DArg—Pro—Lys—Pro—DPhe—Gln—DTrp—Phe—DTrp—Leu—Leu—NH₂ |
| E | Arg—DPro—Lys—Pro—Gln—Gln—DTrp—Phe—DTrp—Leu—Met—NH₂ |
| F | DPro—Gln—Gln—DTrp—Phe—DTrp—DTrp—Met—NH₂ |
| G | Arg—DTrp—MePhe—DTrp—Leu—Met—NH₂ |
| H | DArg—DPro—Lys—Pro—Gln—Gln—DPhe—Phe—DHis—Leu—Met—NH₂ |
| J | HArg—Gly—Gln—DTrp—Phe—Gly—Asp—(OtBu)₂ |
| K | DPro—Gln—Gln—DTrp—Phe—DTrp—Leu—Met—NH₂ |

References

1. Rozengurt, E., Legg, A. and Pettican, P. (1979) Proc. Natl. Acad. Sci. U.S.A. 76, 1284–1287.
2. Rozengurt, E. and Sinnett-Smith, J. (1983) Proc. Natl. Acad. Sci. U.S.A. 80, 2936–2940.
3. Nilsson, J., von Euler, A. M. and Dalsgaard, C.-J. (1985) Nature 315, 61–63.
4. Payan, D. G. (1985) Biochem. Biophys. Res. Commun. 130, 104–109.
5. Singh, P., Walker, P., Townsend, C. M. Jr and Thompson, J. C (1986) Cancer Res. 46, 1612–1616.
6. Anastasi, A., Erpsamer, V. and Bucci, M. (1971) Experientia 27, 166–167.
7. McDonald, T. J., Jornvall, H., Nilsson, G., Vagne, M., Ghatei, M., Bloom, S. R. and Mutt, V. (1979) Biochem. Biophys. Res. Commun. 90, 227–223.
8. Wharton, J., Polak, J. M., Bloom, S. R., Ghatei, M. A., Solicia, E., Brown, M. R. and Pearse, A. E .G. (1978) Nature 273, 769–770.
9. Moody, T. W. and Pert, C. B. (1979) Biochem. Biophys. Res. Commun. 90, 7–14.
10. Minamino, N., Kargawa, K. and Matsuo, H. (1983) Biochem. Biophys. Res. commun. 114, 541–548.
11. Minamino, N., Kanagawa, K. and Matsuo, H. (1984) Biochem. Biophys. Res. Commun. 119, 14–20.
12. Minamino, N., Sudoh, T., Kangawa, K. and Matsuo, H. (1985) Biochem. Biophys. Res. Commun. 130, 685–691.
13. Zachary, I. and Rozengurt, E. (1985) Proc. Natl. Acad. Sci. U.S.A. 82, 7616–7620.
14. Brown, K. D., Blay, J., Irvine, R. F., Heslop, J. P. and Berridge, M. J. (1984) Biochem. Biophys. Res. Commun. 123, 377–384.

15. Wakelam, M. J. O, Davies, S. A., Houslay, M. D., McKay, I., Marshall, C. J. and Hall, A. (1986) Nature 323, 173–176.
16. Mendoza, S. A., Schneider, J. A., Lopez-Rivas, A., Sinnett-Smith, J. W. and Rozengurt, E. (1986) J. Cell Bio. 102, 2223–2233.
17. Zachary, I., Sinnett-Smith, J. W. and Rozengurt, E. (1986 ) J. Cell Biol. 102, 2211–2222.
18. Moody, T. W., Pert, C. B., Gazdar, A. F., Carney, D. N. and Minna, J. D. (1981) Science 214, 1246–1248.
19. Wood, S. M., Wood, J. R., Ghatei, M. A., Lee, I. C., O'Shaughnessy, D. and Bloom, S. R. (1981) J. Clin. Endocrin. Metab. 53, 1310–1312.
20. Erisman, M. D., Linnoila, R. I., Hernandez, O., DiAugustime, R. P. and Lazarus, L. H. (1982) Proc. Natl. Acad. Sci. U.S.A. 79, 2379–2383.
21. Roth, K. A., Evans, C. J., Weber, E., Barchas, J. D., Bostwick, D. G. and Bersch, K. G. (1983) Cancer Res. 43, 5441–5415.
22. Cuttita, F., Carney, D. N., Mulshine, J., Moody, T. W., Fedorko, J., Fischler, A. and Minna, J. D., (1985) Nature 316, 823–826.
23. Pilch, P. F. and Czech, M. P. (1979) J. Biol. Chem. 254, 3375–3381.
24. Massaque, J., Guilletta, B. J. and Czech, M. P. C. (1981) J. Biol. Chem. 256, 2122–2125.
25. Glenn, K., Bowen-Pope, D. F. and Ross, R. (1982) J. Biol. Chem. 257, 5172–5176.
26. Wood, C. L. and O'Dorisio, M. S. (1985) J. Biol. Chem. 260, 1243–1247.
27. Brenner, M. B., Trowbridge, I. S. and Strominger, J. L. (1985) Cell 40, 183–190.
28. Sorensen, P., Farber, N. M. and Krystal, G. (1986) J. Biol. Chem. 261, 9094–9097.
29. Rozengurt, E., Brown, K. D. and Pettican, P. (1981) J. Biol. Chem. 256, 716–722.
30. Rozengurt, E., Collins, M., Brown, K. D. and Pettican, P. (1982) J. Biol. Chem. 257, 3680–3686.
31. Laemmli, U. K. (1970) Nature 227, 680–685.
32. O'Farrel, P. H. (1975) J. Biol. Chem. 250, 4007–4021.
33. Todaro, G. J. and Green, H. (1963) J. Cell Boil. 17, 299–313.
34. Dicker, P. and Rozengurt, E. (1980) Nature 287, 607–612.
35. Jensen, R. T., Jones, S. W., Folkers, K. and Gardner, J. D. (1984) Nature 309, 61–63.
36. Zachary, I. and Rozengurt, E. (1986) Biochem. Biophys. Res. Commun. 137, 135–141.
37. Rozengurt, E., Stroobant, P., Waterfield, M. D., Deuel, T. F. and Keehan, M. (1983) Cell 34, 265–272.
38. Dicker, P. and Rozengurt, E. (1978) Nature 276, 723–726.
39. Wray, W., Boulikas, T., Wray, V. P. and Hancock, R. (1981) Analy. Biochem. 118, 197–203.

We claim:

1. A compound of the formula D-Arg-X-Lys-Pro-Y-Gln-D-Trp-Phe-D-Trp-Leu-Leu-$NH_2$ wherein X is D-Pro or Pro and Y is [D-Phe,] D-Trp [,DTyr or Me Phe, with the proviso that when X is Pro, Y is not D-Phe].

2. A pharmaceutical composition for the treatment of small cell lung cancer in humans, said composition comprising an effective amount to inhibit said small cell lung cancer of a compound according to claim 1 together with a parenterally acceptable carrier or diluent.

3. A method for the treatment of small cell lung cancer in humans which method comprises parenteral administration to a patient in need of such treatment of an effective amount of a compound according to claim 1 to inhibit said small cell lung cancer.

* * * * *